US007981461B2

(12) United States Patent (10) Patent No.: US 7,981,461 B2
Georgette et al. (45) Date of Patent: Jul. 19, 2011

(54) METALLIC BONE IMPLANT HAVING IMPROVED IMPLANTABILITY AND METHOD OF MAKING THE SAME

(76) Inventors: Frederick S. Georgette, West Bloomfield, MI (US); Lee Allen Stouse, Brighton, MI (US)

( * ) Notice: Subject to any disclaimer, the term of this patent is extended or adjusted under 35 U.S.C. 154(b) by 1811 days.

(21) Appl. No.: 11/046,938

(22) Filed: Jan. 31, 2005

(65) Prior Publication Data

US 2005/0171615 A1 Aug. 4, 2005

Related U.S. Application Data

(60) Provisional application No. 60/540,433, filed on Jan. 30, 2004.

(51) Int. Cl.
*B05D 3/12* (2006.01)
*B05D 5/02* (2006.01)
*A61L 27/32* (2006.01)
*A61F 2/28* (2006.01)

(52) U.S. Cl. ...... 427/2.1; 427/2.24; 427/2.25; 427/2.27; 427/256; 623/11.11

(58) Field of Classification Search .................. 427/2.1, 427/2.24, 256; 623/11.11
See application file for complete search history.

(56) References Cited

U.S. PATENT DOCUMENTS

| 4,177,524 | A | 12/1979 | Grell et al. | 3/1.9 |
| 4,379,694 | A | 4/1983 | Riess | 433/201 |
| 4,789,649 | A | 12/1988 | Abert et al. | 501/3 |
| 5,139,424 | A | 8/1992 | Yli-Urpo | 433/201.1 |
| 5,205,921 | A | 4/1993 | Shirkanzadeh | 205/318 |
| 5,226,260 | A | 7/1993 | Mar et al. | 51/319 |
| 5,251,468 | A | 10/1993 | Lin et al. | 72/53 |
| 6,069,295 | A * | 5/2000 | Leitao | 623/11.11 |
| 6,136,369 | A | 10/2000 | Leitao et al. | 427/2.27 |
| 6,143,948 | A | 11/2000 | Leitao et al. | 623/11 |
| 6,344,061 | B1 | 2/2002 | Leitao et al. | 623/23.5 |
| 6,521,264 | B1 | 2/2003 | Lacout et al. | 424/602 |
| 6,530,951 | B1 | 3/2003 | Bates et al. | 623/1.45 |
| 6,582,228 | B2 | 6/2003 | Ricci et al. | 433/173 |
| 6,617,027 | B2 | 9/2003 | Kim et al. | 428/411.1 |
| 2003/0031983 | A1 | 2/2003 | Kotte et al. | 433/201.1 |

FOREIGN PATENT DOCUMENTS

DE 19830530 A1 * 1/2000

OTHER PUBLICATIONS

International Search Report and Written Opinion dated May 4, 2006 from corresponding International Application No. PCT/US05/02626.

* cited by examiner

*Primary Examiner* — Timothy H Meeks
*Assistant Examiner* — Cachet I Sellman
(74) *Attorney, Agent, or Firm* — Young & Basile, P.C.

(57) ABSTRACT

An implantable device composed of a biocompatible material having an enhanced surface topography that has an implanted calcium ion concentration and method of making the same.

8 Claims, 4 Drawing Sheets

METALLIC BONE IMPLANT HAVING IMPROVED IMPLANTABILITY AND METHOD OF MAKING THE SAME

The present application claims priority to U.S. Provisional Application No. 60/540,433 filed Jan. 30, 2004 entitled "METHOD FOR IMPROVING IMPLANTABILITY OF METALLIC BONE IMPLANTS."

The invention pertains generally to methods for preparing bone implants, particularly metallic bone implants; such implants would be used, for example, in orthopedic, spinal, and dental implants, and more particularly to such a method comprising the ordered steps of improving a desired metallic bone implant having an enhanced surface area, obtained, for instance, by subjecting a desired metallic bone implant to a surface enhancement treatment, and thereafter implanting calcium ions on the enhanced surface of the metallic bone implant. The present invention also pertains to bone implants having enhanced surfaces possessing implanted calcium ions capable of enhanced cell growth and support.

BACKGROUND

Known and in clinical use for many years, dental implants are metal fixtures that, when placed in the jawbone, function as "roots" for replacement teeth. Metal alloys, including for example, titanium alloys such as Ti-6Al-4V and Ti—Al-2.5Fe, Co—Cr—Mo, etc., are known biocompatible materials commonly employed for dental implants. Implants have also been used successfully in various bone implantation procedures including, but not limited to, spinal, hip, and knee procedures, as well as various limb salvage and anchoring operations.

It is known that the surface roughening of metallic implants, by mechanical or chemical processes, increases their in situ fixation by providing a greater surface area for osseointegration. However, some commonly employed roughening methods, including glass beading and grit blasting, leave embedded roughening media in the surface of the implant. There is mounting evidence that these embedded media contribute to eventual osteolysis, that is, bone readsorption.

Alternatively, it is known to provide implants with a porous surface coating, the presence of the pores providing an increased surface area or bone ingrowth into the implant. Such coatings include those achieved by sintering metal particles to the surface of a selected metallic implant at a density sufficient to leave numerous pores in the coating, and high-temperature sprayed metallic coatings, according to which metal particles are heated and thereafter deposited on the surface of the implant by high-speed bombardment.

Though titanium is a biocompatible metal, osseointegration around titanium is known to be inferior to that around bioactive ceramics, such as calcium phosphate. Accordingly, it is known to provide titanium dental implants with a coating of calcium phosphate, including, for example, hydroxyapatite $(Ca_{10}(PO_4)_6(OH)_2)$. However, apatite-coated metal implants are also attended by drawbacks, including fracturing and, in some instances, bacterial colonization.

There thus continues to exist a need for metallic bone implants with improved implantability and methods for effectively making the same.

SUMMARY

Disclosed herein is an implantable device comprising a biocompatible material having an enhanced surface area The enhanced surface area is characterized by a roughened region. The enhanced surface area also has a calcium ion concentration sufficient to permit and/or enhance viability of bone cells in contact with the enhanced surface topography.

Also disclosed herein is a method for improving the implantability of metallic bone implants. The method comprises the ordered steps of providing a desired bone implant having an enhanced surface area, obtained, for instance, by subjecting the implant to a surface roughening treatment or by applying a porous surface coating, and thereafter implanting calcium ions on the enhanced surface of the metallic bone implant material.

According to one embodiment of the method disclosed herein, the enhanced surface area of the implant material or device is obtained by a surface roughening comprising blasting the metallic bone implant with a blast media characterized by its solubility in nitric acid, and further comprising the step of dissolving substantially all of the blast media remaining on the roughened surface of the implant using a solution comprising nitric acid. According to this embodiment, the blast media comprises calcium phosphate. Also per this embodiment, the roughened surface of the implant, created by blasting with calcium phosphate, is characterized by a roughness of 0.5 to 4 microns. This is followed by calcium ion implantation.

According to another embodiment of the method disclosed herein, the enhanced surface area of the implant material or device is obtained in whole or in part by the application of suitable surface coating to the surface of the implant material or device at a density sufficient to leave numerous pores having an average pore size between 50 and 1000 microns on the surface followed by calcium ion implantation.

According to another feature hereof, the method may further comprise the steps of ultrasonically cleaning and/or passivation of the bone implant following the surface roughening treatment and preceding the ion implantation step.

BRIEF DESCRIPTION OF THE FIGURES

The inventive methodology will be better understood with reference to the following written description and drawings, wherein.

DETAILED DESCRIPTION

Figure 1:
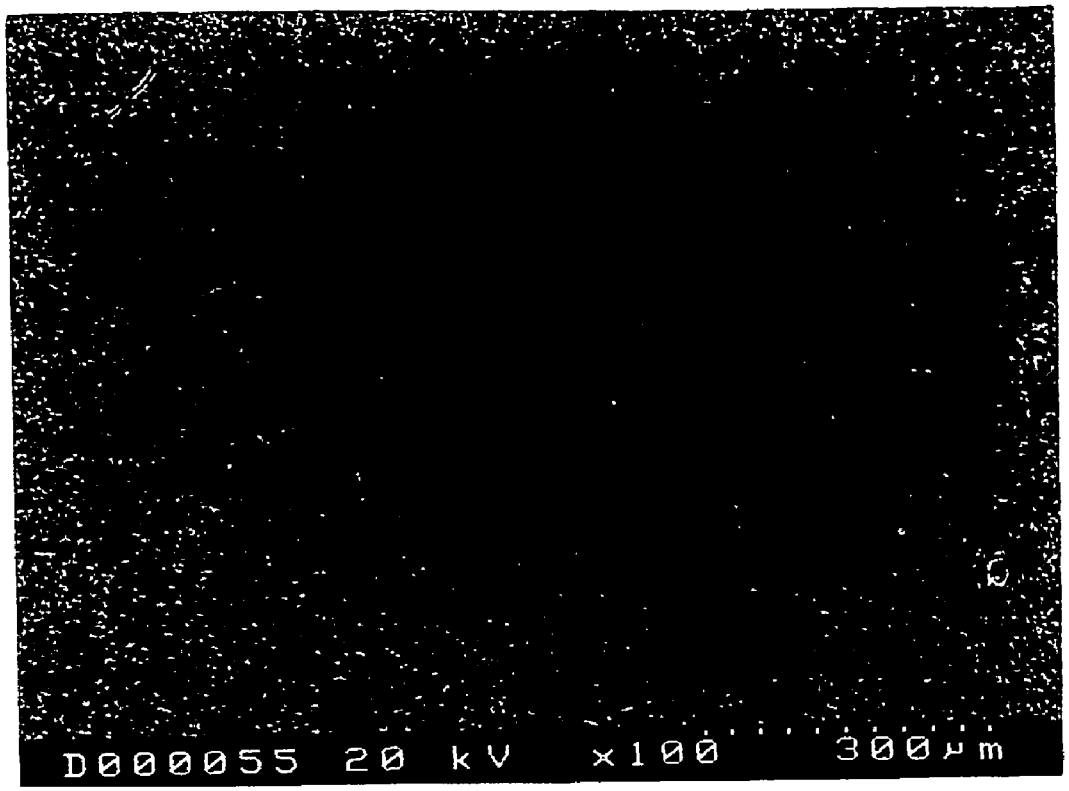
FIG. 1 comprises a reproduction of an SEM micrograph, taken at 100×, showing the unenhanced surface of an "as machined" metallic Ti-6Al-4V implant material.

Disclosed herein is an implantable device comprising a biocompatible material having an enhanced surface topography. The roughened surface has a calcium ion concentration sufficient to permit and/or enhance viability of bone cells in contact with the enhanced surface topography. The roughened surface having the aforementioned calcium ion concentration gives rise to a modified surface supportive of integrated bone formation that may be characterized by increased presence of suitable bone cells in integrated relationship with the roughened surface in in vivo application.

In its most general depiction, the implantable device as disclosed herein can be composed of a biocompatible material having at least a portion of its outer surface characterized as an enhanced surface area The enhanced surface area has a roughened surface region configured to permit enhanced fixation of the implant device into bone tissue and integration of suitable osseogenic cells into intimate contact with the enhanced surface area. It is contemplated that the enhanced surface area may exhibit microscopic roughening, macroscopic roughening, or a mixture of the two. As used herein, the term "microscopic texturing or roughening" is defined as surface roughness typically measured as 10 microns (Ra) or less. The term "macroscopic texturing or roughening", as used herein, is defined as surface roughness manifesting as pores having an average pore size between 50 and 1000 microns. In situations where the macroscopic texturing is accomplished by surface roughening techniques, it is contemplated that the surface will have a nonporous surface roughness greater than 10 microns (Ra).

The biocompatible material can be formed in any suitable shape or configuration for its intended end use. Without being so limited, it is contemplated that the device can be used in a wide variety of biomedical applications such as surgery, bone replacement, and prosthodontics. Nonlimiting examples of procedures where implants as disclosed herein can be employed include dental implants, implants used in the spine, hip, knee, as well as other suitable bone regions. Thus the implant can be configured as a suitable rod, pin, plate, or other device desired for bone implantation. In a more particular application, it is contemplated that the implantable device can be utilized effectively in applications requiring relatively small implants that must be configured to bear significant stress loads as can be present in the mandible and maxillary bones. Thus, the device can be effectively used as a dental implant article. Other uses, configurations, and applications are contemplated. Nonlimiting examples of such include use as a part of limb salvage procedures as well as use as support lattice for bone regrowth and reconstruction.

The substrate of the implantable device can be composed of various biocompatible materials. These materials include metals, in particular biocompatible metals, such as titanium, tantalum, niobium, zirconium, cobalt, and alloys thereof, as well as stainless steel. Nonlimiting examples of alloys include titanium alloys such as Ti-6Al-4V and Ti—Al-2.5Fe, as well as alloys such as Co—Cr—Mo, etc. The material of choice will be one that is capable of maintaining beneficial ions such as calcium within the material substrate lattice. Thus, it is contemplated that other classes of biocompatible materials such as inorganic, natural, and synthetic polymers, ceramics, and the like, may be employed as at least part of the biocompatible material in certain end use applications. Nonlimiting examples of suitable polymers include polyethylene, PEEK, polysulfone, and polytetrafluoroethylene. Nonlimiting examples of ceramic materials include alumina or zirconia as well as composite materials.

The biocompatible material will have a portion of its outer surface having an enhanced surface area The enhanced surface area will have a roughened surface region configured to permit fixation of the implant device into bone tissue. It is contemplated that the enhanced surface topography can exhibit microscopic texturing, macroscopic texturing, or some combination of both.

Microscopically textured surfaces will exhibit regions of topographic complexity or roughness such as peaks and valleys to which a portion or portions of various osseogenic cells can adhere and conform. Microscopic surface roughness can be defined as the measure of vertical deviations in a surface region when traversing the surface of the implant material. This value can be expressed as "average roughness" (Ra), which is calculated as the total area of peaks and valleys divided by the observation length. Peak and valley area can be determined by measuring instruments such as a profilometer. The average roughness for microscopically roughened surfaces employed in the implant device disclosed herein will be between 0.5 and 10 microns (Ra). Various techniques can be employed to provide microscopically textured surfaces. Examples of these will be discussed in detail subsequently.

Alternately, the enhanced surface topography can exhibit macroscopic porosity. Macroscopic porosity can be achieved by any suitable macroscopic texturing method. The pore size can be one suitable for achieving enhanced bone cell integration. It is contemplated that average pore sizes of between 50 and 1000 microns can be advantageously utilized.

Macroscopic texturing can be accomplished by a variety of procedures. These include, but are not limited to, sintering, plasma spraying, and deposition of suitable materials on the surface of the biocompatible material. Such processes can be collectively called porous deposition techniques.

It is also contemplated that macroscopic texturing can include processes that create macroscopic landscapes having textures other than porous. These other macroscopic texturing techniques can include, but are not limited to, machining, laser texturing, and chemical etching, with texture topography sizes above the approximate 10 micron (Ra) threshold defining microscopic texturing.

The implantable device as disclosed herein also has an implanted calcium ion ($Ca^{2+}$) concentration in the biocompatible material. Implanted calcium ion concentration can be expressed as a planar dose per unit of area. The planar dose contemplated herein can be any dose up to that which initiates or results in formation of calcium oxide on the surface and in the near surface region of the implant device. This upper threshold varies from material to material. By way of example only, it is contemplated that the implanted calcium ion concentration in the implant material can be between $0.5\ E^{17}/cm^2$ to $10\ E^{17}/cm^2$. Other concentration levels can be employed, both above and below this exemplary concentration range, as desired or required within the previously mentioned limitations.

It is also within the purview of this invention that the implant can include discrete regions of roughening and macroscopic porosity on a single implant as desired or required for a given application.

The implanted calcium ion concentration will be present in the biocompatible material at the surface and near surface region. As used herein, the term "near surface region" is taken to mean the region proximate to the outer surface of the biocompatible bone material to a depth of approximately 5,000 angstroms. Typically, it is contemplated that the calcium ion concentration will be present to a depth of between 100 and 2500 angstroms, with more specific depths being between 1,000 and 2500 angstroms. Depth of penetration can vary depending upon the biocompatible material employed. It is contemplated that alloys such as Ti-6Al-4V can have depth of penetration typically between 1500 and 2500 angstroms while alloys such as Co—Cr—Mo will be less with depths between 1000 and 2000 being typical.

The calcium ion concentration can be implanted in the surface and near surface of the biocompatible material by a suitable ion implantation method. Ion implantation has been performed on various materials. However, calcium ion implantation has not been performed on biocompatible materials having suitably macroscopically textured and/or microscopically textured surfaces. Thus, it is contemplated that the calcium ion concentration in the surface and near surface region of the biocompatible material will vary based upon differences in topography. The sides of the asperities typically exhibit lower calcium ion concentration than the peaks and valleys. Typically, the calcium ion concentration will be present as a cosine function based on the angle of incidence of calcium ion implantation.

Without being bound to any theory, it is believed that the unique configuration of implanted calcium ion concentration on the macroscopically and/or microscopically textured surface provides an implant having characteristics that promote enhanced fixation of the implant in surrounding bone tissue with better osseointegration and more complete healing of the implant site.

Also disclosed herein is a method or methods for producing an implantable device suitable for use as a bone implant, for example dental implants, employed in the mandible and maxilla regions of a patient as well as implants in anatomical regions such as the spine, hip, knee, etc. The device and method provides improved in situ fixation of the resulting implant in the surrounding bone tissue. The resulting implantable device has enhanced surface topography that includes implanted calcium ($Ca^{2+}$) ions in the enhanced topography that, in certain instances, can lead to augmented bone growth and support around the implant.

According to a first embodiment, the method disclosed herein essentially comprises the ordered steps of subjecting a desired bone implant to a surface texturing treatment and thereafter implanting calcium ions on the textured surface of the bone implant.

According to a second embodiment, the method essentially comprises ordered steps of providing a porous coating on the surface of a desired implant to enhance the surface area and thereafter implanting calcium ions on the enhanced surface of the bone implant.

The implant employed in the method contemplated herein can be composed in whole or in part of the biocompatible materials previously. These materials include metallic materials, such as, without limitation, at least one of titanium, niobium, zirconium, tantalum, cobalt, and alloys thereof, as well as stainless steel. Nonlimiting examples of suitable metal alloys include alloys such as Ti-6Al-4V and Ti—Al-2.5Fe. Other nonlimiting examples of suitable metal alloys include Co—Cr—Mo, stainless steel, and the like.

According to a first embodiment of the method disclosed herein, the enhanced surface topography of the biocompatible material of the implantable device can be achieved by a macroscopic texturing or surface roughening step comprising any of several finishing techniques known to those skilled in the art. Such techniques include, but are not limited to, acid etching, surface blasting with aluminum ($Al_2O_3$) or titanium oxide, grit, (so-called "grit blasting"), and surface blasting with glass beads (so-called "glass beading"), glass bead blasting, or blasting with resorbable blast medium such as calcium phosphate.

Because conventional grit blasting and glass beading techniques have been associated with osteo devices in in situ dental implants, the method may also include processes for the reduction or removal of at least a portion of the residual material remaining after grit blasting or glass beading.

It is also contemplated that the surface finishing techniques disclosed herein can employ, in total or in part, the use of resorbable blast media According to this technique, the surface of an implantable device or suitable bone implant is grit blasted with a resorbable material such as calcium phosphate. The surface roughened material is then subjected to a process whereby the calcium phosphate blasting material is removed, typically by dissolution. The surface-roughened implantable device can be contacted by a material that results in the dissolution of any calcium phosphate resorbable blast media associated with the roughened surface. Contact can occur by any suitable method such as immersion. The dissolving material of choice will be one capable of dissolving residual calcium phosphate to accomplish effective removal of calcium phosphate in association with a roughened surface such as strong acids. Suitable acids will be those that can accomplish dissolution while remaining inert to adverse interaction with the biocompatible material. One nonlimiting example of a suitable acid is nitric acid employed as a passivation medium.

The implant having the prepared enhanced surface topography is subjected to suitable calcium ion implantation procedures to provide an implanted calcium ion concentration sufficient to improve viability of bone cells in contact with the enhanced surface topography.

Calcium ion implantation can be accomplished by any suitable method to achieve a desired calcium ion concentration defined in terms of planar dose. A nonlimiting example of planar dose is between $0.5\,E^{17}/cm^2$ and $10\,E^{17}/cm^2$. However, it is contemplated that greater and lower doses can be utilized depending on the end use application. Thus the prepared implant can be subjected to calcium ion implantation in which the calcium ions are incorporated into the metal lattice by accelerating the ionized calcium atoms through an electrostatic field and onto the target biocompatible material. According to the procedure, the depth of implantation depends upon such variables as the chemistry of the target material, the implantation dose, and the energy of the electrostatic field. Accordingly, calcium ions are deposited onto a metal substrate with a suitable acceleration energy, for example, between 15 and 40 keV, and an ion beam current density of between 30 and 60 microA/cm$^2$ in a neutral atmosphere such as krypton to achieve a suitable planar dose. It is contemplated that other ion implantation processes can be implemented in the present invention.

It is also contemplated that the implant may be subjected to various additional optional steps at various stages of the process. Such steps include but are not limited to cleaning steps and the like. In one such cleaning step various residual materials can be removed from contact with the roughened surface. Suitable cleaning processes can include but need not be limited to ultrasonic cleaning in which the implantable device is subjected to bombardment by ultrasonic waves in any of a variety of solutions as would be known to those skilled in the art. When the RBM technique is employed, it is contemplated that the ultrasonic cleaning step will occur subsequent to the passivation step.

To further illustrate the invention disclosed herein, the following nonlimiting examples are provided.

EXAMPLE I

A study of microscopic surface roughening techniques was conducted to ascertain the effectiveness of such processes. Metallic coupons of Ti-6Al-4V were prepared. A series of "as machined" coupons were isolated from further processes. The "as machined" or control coupons were analyzed to ascertain baseline data. The coupons were evaluated using scanning electron micrograph (SEM) analysis using an AMRAY 1645/SEM set for energy dispersive X-ray (EDAX) analysis. SEM micrographs were taken at 100× to 400× to assess the surface appearance.

Surface roughness measurements of coupons were made using a MITUTOYO SURFTEST 211 surface roughness profilometer commercially available from Mitotoyo American Corporation. The methodology employed was that outlined in the operating instructions of the SURFTEST 211 device An average of five readings were performed for the surface test. A representative micrograph of the as machined surface that was used as the control is reproduced at FIG. 1. The surface analysis data was collected and is presented in FIG. 7. Analysis indicated an average roughness of 1.32 microns (Ra) with a standard deviation of +/−0.2 microns.

EXAMPLE II

Metallic material coupons containing Ti-6Al-4V were blasted with glass bead material using a TRINCO 20/CPH blaster commercially available from Trinity Tool Company of Fraser, Mich. The glass bead media employed was characterized by particle sizes ranging from −100 to +170 mesh. Subsequent to blasting, the roughened surface of the sample material was ultrasonically cleaned.

The thus prepared surface of the sample was evaluated using SEM analysis as outlined in Example 1. SEM micrographs were taken at 100× to visually assess the surface appearance of the roughened implant. Roughness measurements of the roughened dental implant material were made as outlined in Example 1.

Figure 2:
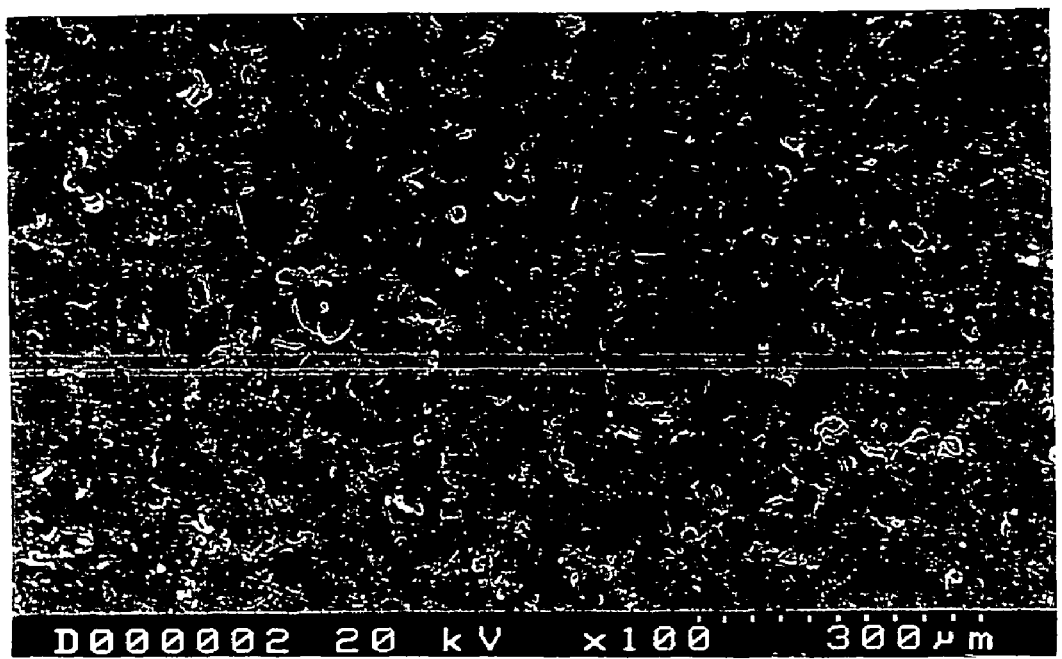
FIG. 2 comprises a reproduction of an SEM micrograph, taken at 100×, showing the enhanced surface of a metallic Ti-6Al-4V implant material obtained by a glass bead procedure suitable to the method disclosed herein.

FIG. 2 is a micrograph of the glass-bead roughened surface of the dental implant. The surface appeared slightly smoother than the control surface. No entrapped media was observed on the particular micrograph. However, entrapped media has been reported using this and a similar processes.

Figure 7:
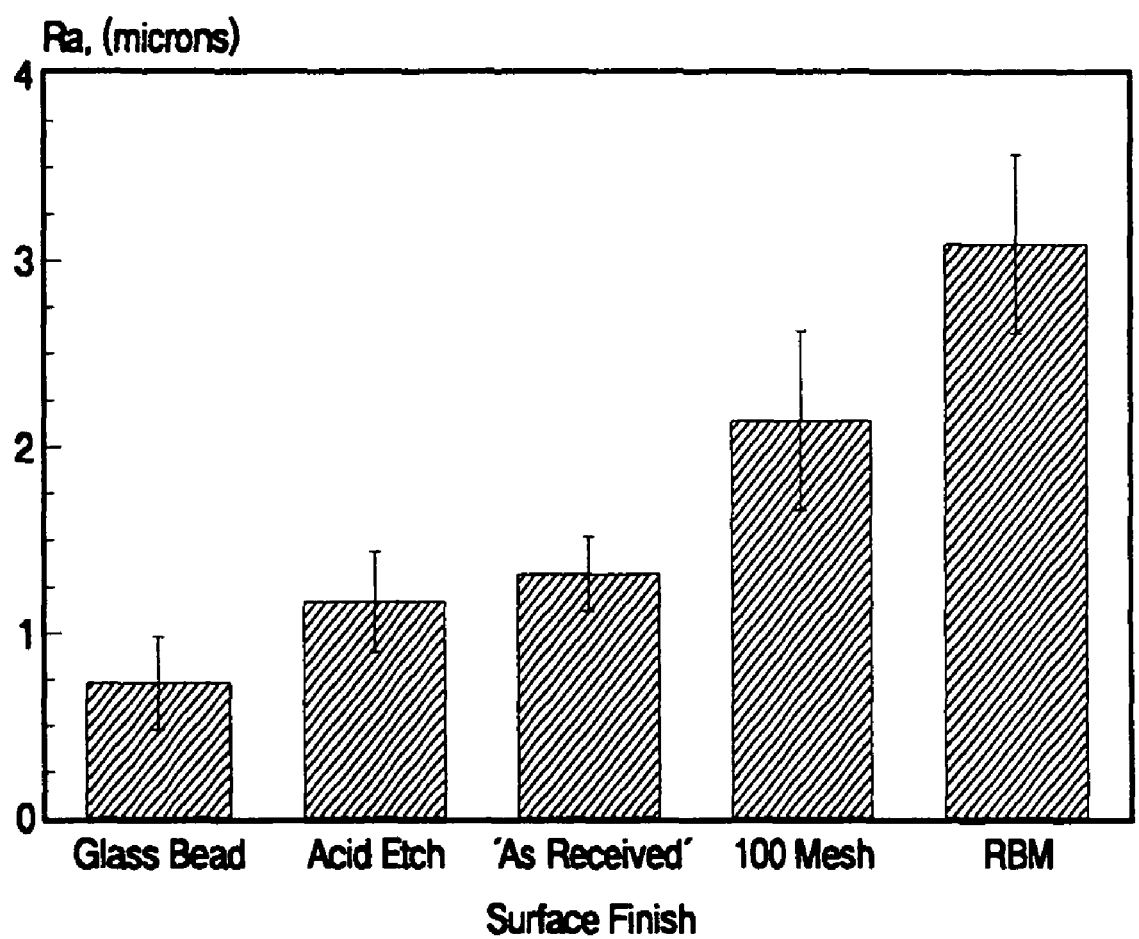
FIG. 7 is a comparative bar chart depicting surface roughness methods for each of five metallic implant material samples shown in the micrographs of FIGS. 1-5.

As shown in FIG. 7, surface analysis of the glass-bead treated surface indicates an average roughness of 0.73 microns (Ra) with a standard deviation of +/−0.25 microns. Comparison of this data with the data derived from the as machined or control samples of Example I supports the conclusion that glass bead blasting procedures such as that employed in this Example reduces surface roughness, possibly through reduction of peak height.

EXAMPLE III

Metallic coupons comprising Ti-6Al-4V were treated by acid etching accomplished by immersing the coupons in a solution of nitric acid, hydrofluoric acid, and water. The treated coupons were then cleaned using de-ionized water and ultrasonic cleaning.

The thus prepared surface of the metal coupons were evaluated using SEM analysis as outlined previously. SEM micrographs were taken at 100× to visually assess the surface appearance of the roughened dental implant. Roughness measurements of the roughened metallic coupon material were conducted according to the procedures outlined in Example 1.

Figure 3:
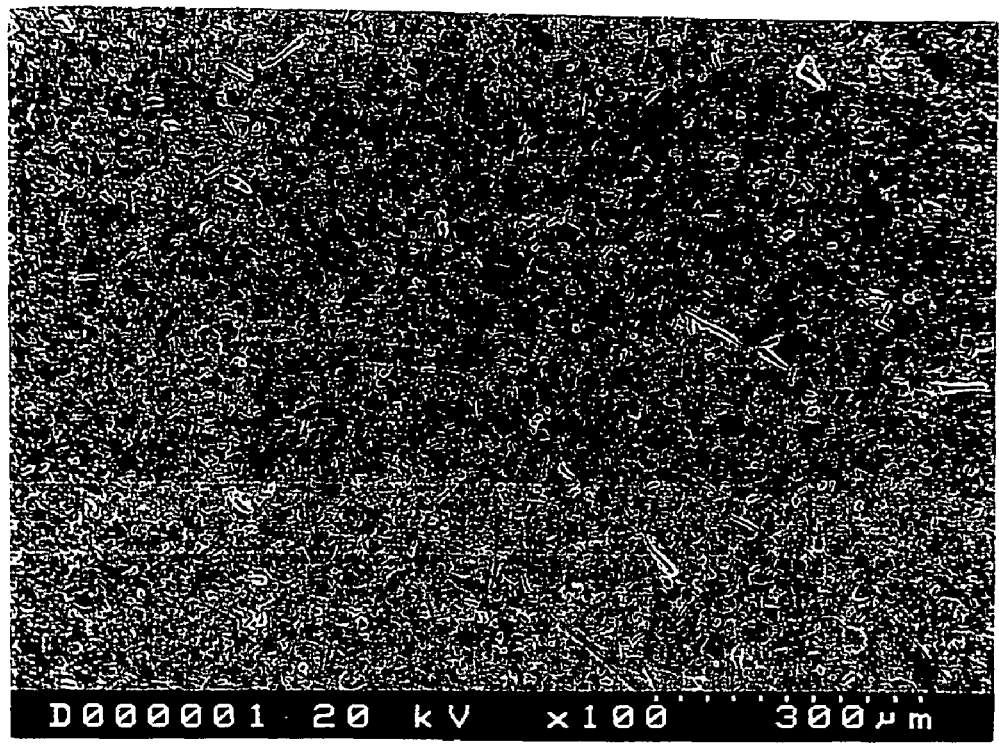
FIG. 3 comprises a reproduction of an SEM micrograph, taken at 100×, showing the enhanced surface of a metallic Ti-6Al-4V implant material obtained by an acid-etching procedure suitable to the method disclosed herein.

FIG. 3 is a representative micrograph of the acid-etched surface of metal coupons. As shown in FIG. 7, surface analysis of the acid-etched surface indicated an average roughness of 1.17 microns (Ra) with a standard deviation of +/−0.27 microns. The results support that conclusion that acid etching procedures as outlined in this example serve to reduce the surface roughness of the metallic coupon, possibly by functioning to reduce the peak height.

EXAMPLE IV

Metallic coupons composed of Ti-6Al-4V were blasted with aluminum oxide ($Al_2O_3$) using the TRINCO/CPH blaster outlined in Example II adjusted to achieve maximum roughness. The $Al_2O_3$ media was characterized by a mean particulate size of approximately 100 mesh.

Subsequent to blasting, the roughened surfaces of the metal coupons were ultrasonically cleaned. The prepared surface of the coupons was evaluated by SEM analysis as outlined in Example 1. SEM micrographs were taken at 100× to visually assess the surface appearance of the roughened coupon material. Roughness measurements of the roughened coupon material were made as outlined in Example 1.

Figure 4:
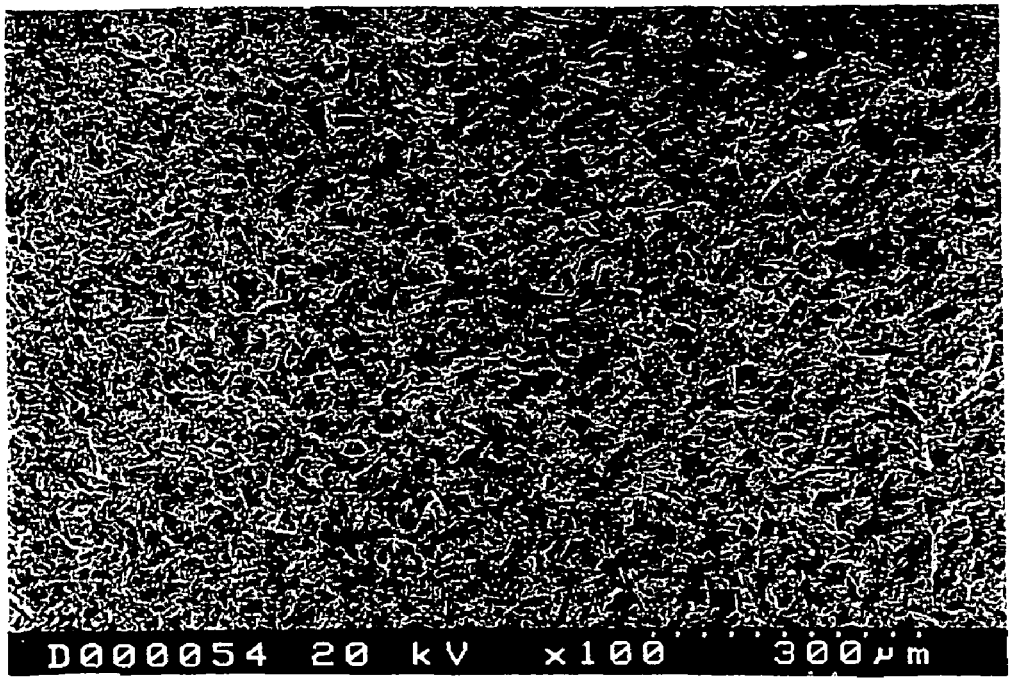
FIG. 4 comprises a reproduction of an SEM micrograph, taken at 100×, showing the enhanced surface of a metallic Ti-6Al-4V implant material obtained by an $Al_2O_3$-blasting procedure suitable to the method disclosed herein.

FIG. 4 is a representative micrograph of the $Al_2O_3$ roughened surface of the coupon material. In comparison to the materials outlined in Examples 1-3, the $Al_2O_3$ roughened surface appears rougher than the surfaces of each of the control, glass-bead treated material, and acid etched sample materials. The SEM set forth in FIG. 4 also evidences regions of charging suggesting that some of the $Al_2O_3$ remained embedded in the implant material subsequent to the ultrasonic cleaning step.

FIG. 7 represents a comparative bar chart of various surface roughness measurements with surface analysis of the $Al_2O_3$ treated surface having an average roughness of 2.14 microns (Ra) with standard deviation of +/− at 0.48 microns.

EXAMPLE V

Metallic coupons composed of Ti-6Al-4V were blasted with calcium phosphate blasting media according to the procedure in Example II. The calcium phosphate blasting media was characterized by particulate size ranging from −40 to +80 mesh.

Thereafter, the roughened surface was passivated in a nitric acid solution of 25-40% nitric acid to dissolve the calcium phosphate blasting media from the surface of the sample material. Subsequent to passivation, the roughened surface of the dental implant material was ultrasonically cleaned.

The thus prepared surface of the sample material was evaluated using the procedures outlined in Example I. SEM micrographs were taken at 100× to visually assess the surface appearance of the roughened sample material.

Surface roughness measurements of the roughened metallic coupons were conducted according to the procedure outlined previously.

Figure 5:
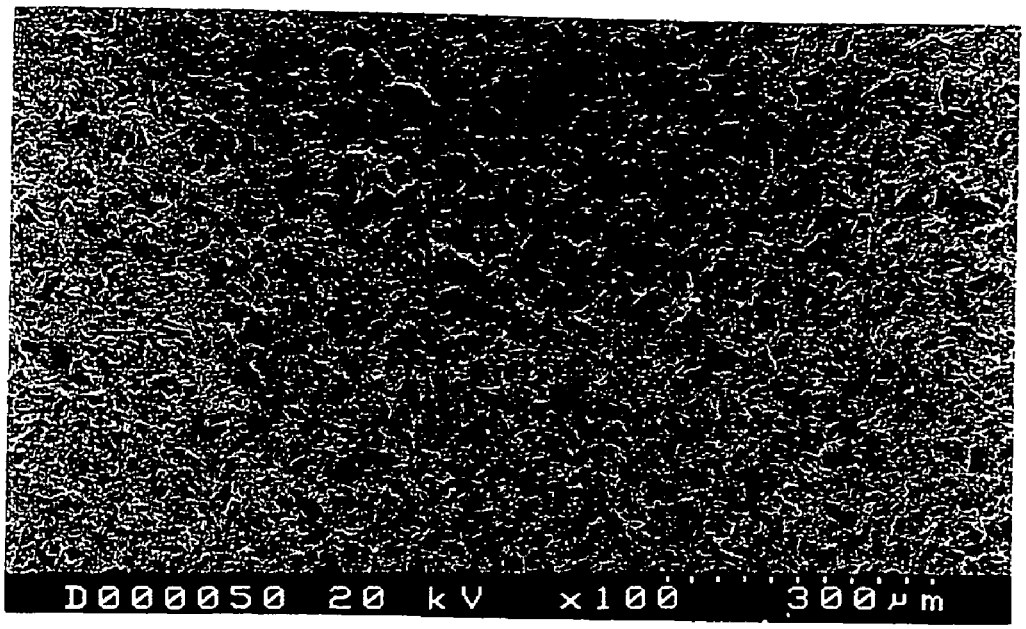
FIG. 5 comprises a reproduction of an SEM micrograph, taken at 100×, showing the enhanced surface of a metallic Ti-6Al-4V implant material obtained by an RBM procedure as disclosed herein.

FIG. 5 is a representative micrograph of the RBM-roughened surface of a representative coupon.

Analysis of the SEM data further reveals that the passivation process successfully removed embedded material from contact with the surface of the metallic coupon. The SEM data indicated that the roughened surface exhibited no charging upon SEM analysis. Charging is a phenomenon created when a nonconductive material is exposed to an SEM beam and is characterized by the appearance of nonconductive material as white with a dark "halo". Absence of this phenomenon is indicative of absence of nonconductive or blast material.

Data comparing surface roughness (Ra) measurements (in microns) for this material was collected and is set forth in FIG. 7. Surface analysis of the RBM-treated surface indicated an average roughness of 3.09 microns (Ra) with a standard deviation of +/−0.48 microns.

Analysis indicates that the RBM-surface treated material exhibited the greatest surface roughness. The material was considerably rougher than surfaces treated by acid etching and glass bead treatment and was significantly rougher than material treated by $Al_2O_3$ blasting without evidence of the charging phenomenon indicative of embedded material.

EXAMPLE VI

Figure 6:
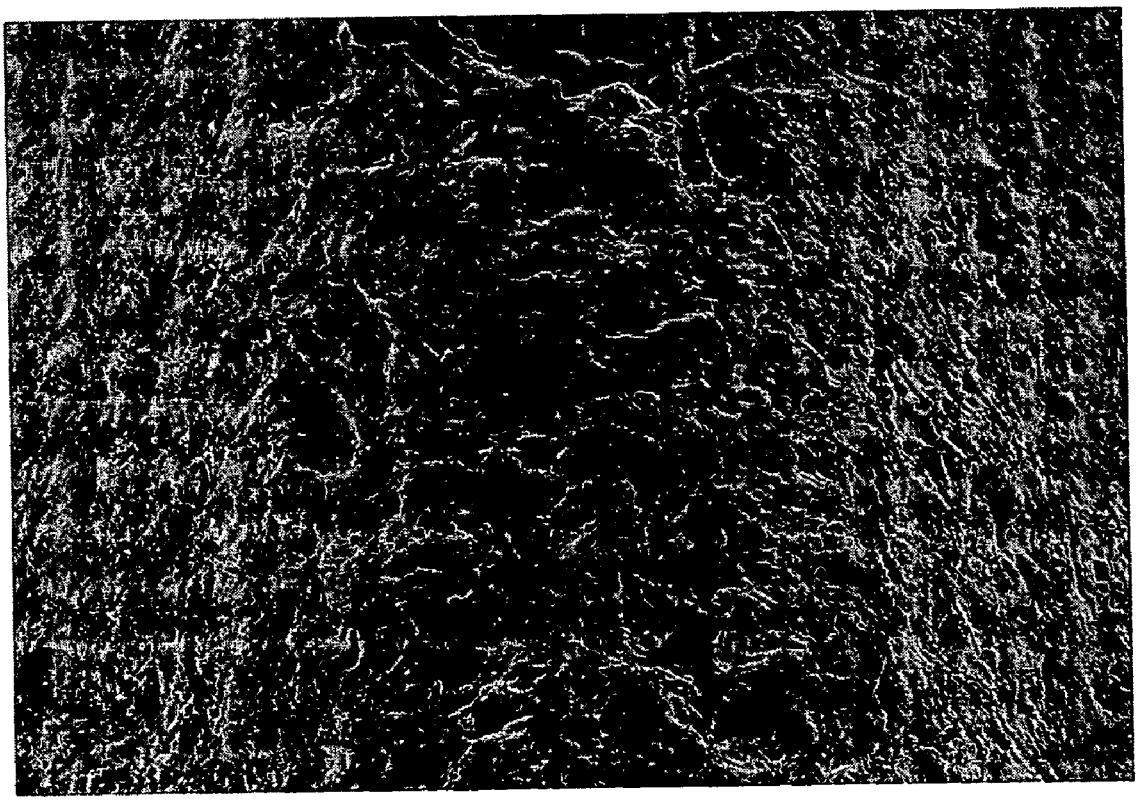
FIG. 6 is a reproduction of an SEM taken at 400× of a metallic Ti-6Al-4V implant prepared by an RBM and subsequent ion implantation.

Dental implants prepared according to the procedure in Example V were subjected to calcium ion implantation to achieve a calcium ion concentration expressed as a planar dose between 0.5 to 1.5 $E^{17}/cm^2$. The implants were analyzed by SEM according to the methods outlined in Example I and did not differ significantly in surface appearance from samples treated with RBM alone as in Example V. A representative SEM is set forth at FIG. 6 taken at 400×.

EXAMPLE VII-XI

Disks composed of Ti-6Al-4V alloy prepared according to the method outlined in Example V were subjected to four different calcium ion implantation doses to assess the effect of calcium ion implantation on cell growth. Planar doses of calcium ions are as outlined in Table 1.

Samples of planar disks were prepared and sterilized in a depyrogenating oven for one hour at 260° C. Each disk was placed in a well of a 6-well cell culture plate. For each set of disks, 4 wells were used on each of two plates. MMG-63 cells, a human bone osteosarcoma adherent cell line (ATCC Catalog #CRL-1427) were cultured in the laboratory and then seeded onto the disks at a concentration of $3.3 \times 10^4$ cells per disk to produce a confluent monolayer in four to seven days.

After allowing the cells to adhere to the disks, culture medium was added to the wells and the plates incubated in an incubator set at 38° C. (5% $CO_2$). For the glass slide control for cell growth, cells were also seated on glass cover slips with a diameter of approximately 1 inch. Cells on the cover slips were observed to be in a confluent monolayer approximately four days later. At this time, all cells were tripsonized and scraped from the surfaces and counted.

Samples for four disks of each condition were pooled so that there were duplicate samples for each condition. Two aliquots of each pooled sample were taken for counting, and the cell counts were averaged. The results are presented in Table 1.

Average viability for the control RBM and ion implanted RBM samples was found to be lower than that of the glass slide. This was not surprising as removal of cells from surfaces required scraping. Lower observed viability is due to the scraping trauma inherent in removing cells from the roughened surfaces.

Based upon the results, it can be concluded that surface-roughened material having high-energy implantation of calcium provided significantly enhanced cell growth over materials not so treated.

TABLE I

| Planar Dose | Average Number of Cells Recovered | Observed Viability % |
| --- | --- | --- |
| 1. Glass slide | $1.4 \times 10^6$ | 94 |
| 2. RBM no ion implantation | $1.3 \times 10^5$ | 47 |
| 3. $1E^{17}$Ca, 20 keV | $4.8 \times 10^5$ | 79 |
| 4. $1.5E^{17}$Ca, 20 keV | $2.5 \times 10^5$ | 80 |
| 5. $0.5E^{17}$Ca, 20 keV | $3.8 \times 10^5$ | 74 |
| 6. $1E^{17}$Ca, 40 keV | $5.7 \times 10^5$ | 78 |

The data indicates that calcium ion implantation significantly increases bone cell viability of the implant material over non-calcium implanted surfaces. Additionally, it can be inferred that increased viabilty will translate to improvements in osseointegration.

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed:

1. A method for producing metallic bone implants, the method comprising the ordered steps of providing a metallic bone implant composed of a biocompatible material with a surface topography exhibiting macroscopic texturing or roughening and thereafter implanting elemental calcium in the form of calcium ions on the enhanced surface of the metallic bone implant material, wherein the step of providing the metallic bone implant with a surface topography comprises subjecting the bone implant to a surface roughening treatment, and wherein the surface roughening treatment step comprises blasting the metallic bone implant with a blast media characterized by its solubility in strong acid, and further comprising the step of dissolving substantially all of the blast media remaining on the enhanced surface area of the bone implant after roughening treatment by using a solution comprising nitric acid.

2. The method of claim 1, wherein the step of providing the metallic bone implant with a surface topography comprises providing a porous metallic surface coating on the bone implant.

3. The method of claim 1, wherein the surface topography of the bone implant is characterized by surface roughness between 0.5 and 4.0 microns (Ra).

4. The method of claim 1 wherein the elemental calcium in the form of calcium ions are implanted at a planar dose of planar dose between 0.5 $E^{17}/cm^2$ and 10 $E^{17}/cm^2$.

5. The method of claim 1 wherein the elemental calcium in the form of calcium ion implantation step comprises depositing the calcium ions deposited onto the surface topography at an acceleration energy between 15 and 40 keV, and an ion beam current density of between 30 and 60 microA/$cm^2$ in a neutral atmosphere.

6. The method of claim 1 wherein the elemental calcium in the form of calcium ion concentration is implanted in the biocompatible material at the surface to a depth of between 100 and 2500 angstroms.

7. The method of claim 1 wherein the surface topography is at least one of a metal, a metal alloy, a ceramic, a natural or synthetic polymer, and composite of any of these materials.

8. The method of claim 1 wherein the biocompatible material is at least one of titanium, niobium, zirconium, tantalum, cobalt, alloys thereof, and stainless steel.

* * * * *